United States Patent [19]
Niebur et al.

[11] Patent Number: 5,491,295
[45] Date of Patent: Feb. 13, 1996

[54] HYBRID CORN PLANT AND SEED

[75] Inventors: William S. Niebur, Victor, France; Raymond D. Riley, Humboldt County; Stephen W. Noble, Polk County, both of Iowa

[73] Assignee: Pioneer Hi-Bred International, Inc., Des Moines, Iowa

[21] Appl. No.: 323,273

[22] Filed: Nov. 22, 1994

Related U.S. Application Data

[63] Continuation of Ser. No. 962,443, Oct. 16, 1992, abandoned, which is a continuation of Ser. No. 649,786, Feb. 1, 1991, abandoned.

[51] Int. Cl.$^6$ ............................. A01H 5/00; A01H 4/00; C12M 5/04
[52] U.S. Cl. .................. 800/200; 800/250; 800/DIG. 56; 47/58; 435/240.4; 435/240.49; 435/240.5
[58] Field of Search ...................................... 800/200, 205, 800/DIG. 56; 47/58.03, 58.05; 435/240.4, 240.49, 240.5

[56] References Cited

U.S. PATENT DOCUMENTS 4,812,599  3/1989  Segebart .

FOREIGN PATENT DOCUMENTS 160390  1/1990  European Pat. Off. ............ 435/172.3

OTHER PUBLICATIONS

Troyer, A. F. (1990) *A Retrospective View of Corn Genetic Resources*, Journal of Heredity, vol. 81, pp. 17–24.
Allard, R. W. (1960) Principles of Plant Breeding, John Wiley & Sons, Inc., pp. 67–69.
PVP Application and PVP Certificate for Inbred Corn Line PHN46.
PVP Application and PVP Certificate for Inbred Corn Line PHN46.
Conger, B. V., et al. (1987) "Somatic Embryogenesis From Cultured Leaf Segments of Zea Mays", *Plant Cell Reports*, 6:345–347.
Duncan, D. R., et al. (1985) "The Production of Callus Capable of Plant Regeneration From Immature Embryos of Numerous Zea Mays Genotypes", *Planta*, 165:322–332.
Edallo, et al. (1981) "Chromosomal Variation and Frequency of Spontaneous Mutation Associated with in Vitro Culture and Plant Regeneration in Maize", *Maydica*, XXVI:39–56.
Green, et al., (1975) "Plant Regeneration From Tissue Cultures of Maize", *Crop Science*, vol. 15, pp. 417–421.
Green, C. E., et al. (1982) "Plant Regeneration in Tissue Cultures of Maize", *Maize for Biological Research*, pp. 367–372.
Hallauer, A. R. et al. (1988) "Corn Breeding", *Corn and Corn Improvement*, No. 18, pp. 463–481.
Meghji, M. R., et al. (1984). "Inbreeding Depression, Inbred & Hybrid Grain Yields and Other Traits of Maize Genotypes Representing Three Eras", *Crop Science*, vol. 24, pp. 545–549.
Phillips, et al. (1988) "Cell/Tissue Culture and in Vitro Manipulation", *Corn & Corn Improvement*, 3rd Ed., ASA Publication, No. 18, pp. 345–387.
Poehlman (1987) *Breeding Field Crop*, AVI Publication Co., Westport, Ct., pp. 237–246.
Rao, K. V. et al., (1986) "Somatic Embryogenesis in Glume Callus Cultures", *Maize Genetics Cooperative Newsletter*, No. 60, pp. 64–65.
Sass, John F. (1977) "Morphology", *Corn & Corn Improvement*, ASA Publication. Madison, Wisconsin, pp. 89–109.
Songstad, D. D. et al. (1988) "Effect of ACC (1–aminocyclopropane–1–carboxyclic acid), Silver Nitrate & Norbonadiene on Plant Regeneration From Maize Callus Cultures", *Plant Cell Reports*, 7:262–265.
Tomes, et al. (1985) "The Effect of Parental Genotype on Initiation of Embryogenic Callus From Elite Maize (Zea Mays L.) Germplasm", *Theor. Appl. Genet.*, vol. 70, pp. 505–509.
Troyer, et al. (1985) "Selection for Early Flowering in Corn: 10 Late Synthetics", *Crop Science*, vol. 25, pp. 695–697.
Umbeck, et al. (1983) "Reversion of Male–Sterile T–Cytoplasm Maize to Male Fertility in Tissue Culture", *Crop Science*, vol. 23, pp. 584–588.
Wright, Harold (1980) "Commercial Hybrid Seed Production", *Hybridization of Crop Plants*, Ch. 8: 161–176.
Wych, Robert D. (1988) "Production of Hybrid Seed", *Corn and Corn Improvement*, Ch. 9, pp. 565–607.

*Primary Examiner*—Gary Benzion
*Attorney, Agent, or Firm*—Pioneer Hi-Bred International, Inc.

[57] ABSTRACT

According to the invention, there is provided a hybrid corn plant, designated as 3394, produced by crossing two Pioneer Hi-Bred International, Inc. proprietary inbred corn lines. This invention thus relates to the hybrid seed 3394, the hybrid plant produced from the seed, and variants, mutants, and trivial modifications of hybrid 3394. This hybrid corn plant is characterized by superior yield for maturity, excellent seedling vigor, very good roots and stalks, and exceptional stay green. It is widely adapted, but performs best in the Central and Eastern Corn Belt.

6 Claims, No Drawings

HYBRID CORN PLANT AND SEED

This application is a continuation of prior application Ser. No. 07/962,443, filed Oct. 16, 1992, now abandoned, which was a continuation of prior application Ser. No. 07/649,786, field Feb. 1, 1991, now abandoned.

FIELD OF THE INVENTION

This invention is in the field of plant breeding, specifically hybrid corn breeding.

BACKGROUND OF THE INVENTION

The goal of plant breeding is to combine in a single variety/hybrid various desirable traits of the parental lines. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and fruit size, is important.

Field crops are bred through techniques that take advantage of the plant's method of pollination. A plant is self-pollinating if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two homozygous lines produces a uniform population of hybrid plants that may be heterozygous for many gene loci. A cross of two plants each heterozygous at a number of gene loci will produce a population of hybrid plants that differ genetically and will not be uniform.

Corn plants (Zea mays L.) can be bred by both self-pollination and cross-pollination techniques. Corn has male flowers, located on the tassel, and female flowers, located on the ear, on the same plant. Natural pollination occurs in corn when wind blows pollen from the tassels to the silks that protrude from the tops of the incipient ears.

The development of corn hybrids requires the development of homozygous inbred lines, the crossing of these lines, and the evaluation of the crosses. Pedigree breeding and recurrent selection breeding methods are used to develop inbred lines from populations. Breeding programs combine desirable traits from two or more inbred lines or various broad-based sources into breeding pools from which new inbred lines are developed by selfing and selection of desired phenotypes. The new inbreds are crossed with other inbred lines and the hybrids from these crosses are evaluated to determine which have commercial potential.

Pedigree breeding starts with the crossing of two genotypes, each of which may have one or more desirable characteristics that is lacking in the other or which complement the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced. $F_1 \rightarrow F_2$; $F_2 \rightarrow F_3$; $F_3 \rightarrow F_4$; $F_4 \rightarrow F_5$, etc.

A hybrid corn variety is the cross of two inbred lines, each of which may have one or more desirable characteristics lacked by the other or which complement the other. The hybrid progeny of the first generation is designated $F_1$. In the development of hybrids only the $F_1$ hybrid plants are sought. The $F_1$ hybrid is more vigorous than its inbred parents. This hybrid vigor, or heterosis, can be manifested in many ways, including increased vegetative growth and increased yield.

The development of a hybrid corn variety involves three steps: (1) the selection of superior plants from various germplasm pools; (2) the selfing of the superior plants for several generations to produce a series of inbred lines, which although different from each other, each breed true and are highly uniform; and (3) crossing the selected inbred lines with unrelated inbred lines to produce the hybrid progeny ($F_1$). During the inbreeding process the vigor of the lines decreases. Vigor is restored when two unrelated inbred lines are crossed to produce the hybrid progeny ($F_1$). An important consequence of the homozygosity and homogeniety of the inbred lines is that the hybrid between any two inbreds will always be the same. Once the inbreds that give the best hybrid have been identified, the hybrid seed can be reproduced indefinitely as long as the homogeneity of the inbred parents is maintained.

A single cross hybrid is produced when two inbred lines are crossed to produce the $F_1$ progeny. A double cross hybrid, is produced from four inbred lines crossed in pairs (A×B and C×D) and then the two $F_1$ hybrids are crossed again (A×B)×(C×D). Much of the hybrid vigor exhibited by $F_1$ hybrids is lost in the next generation ($F_2$). Consequently, seed from hybrid varieties is not used for planting stock.

Hybrid corn seed can be produced by manual detasseling. Alternate strips of two inbred varieties of corn are planted in a field, and the pollen-bearing tassels are removed from one of the inbreds (female). Providing that there is sufficient isolation from sources of foreign corn pollen, the ears of the detasseled inbred will be fertilized only from pollen from the other inbred (male), and the resulting seed is therefore hybrid and will form hybrid plants.

The laborious detasseling process can be avoided by using cytoplasmic male-sterile (CMS) inbreds. Plants of a CMS inbred are fertilized with pollen from another inbred that is not male-sterile. Pollen from the second inbred can contribute genes that make the hybrid plants male-fertile. Usually seed from detasseled normal corn and CMS produced seed of the same hybrid is blended to insure that adequate pollen loads are available for fertilization when the hybrid plants are grown.

Corn is an important and valuable field crop. Thus, a continuing goal of plant breeding is to develop stable high yielding corn hybrids that are agronomically sound. The reasons for this goal are obvious: to maximize the amount of grain produced on the land used and to supply food for both animals and humans.

SUMMARY OF THE INVENTION

According to the invention, there is provided a hybrid corn plant, designated as 3394, produced by crossing two Pioneer Hi-Bred International, Inc. proprietary inbred corn lines. This invention thus relates to the hybrid seed 3394, the hybrid plant produced from the seed, and variants, mutants, and trivial modifications of hybrid 3394. This hybrid corn plant is characterized by superior yield for maturity, excellent seedling vigor, very good roots and stalks, and exceptional stay green. It is widely adapted, but performs best in the Central and Eastern Corn Belt.

DEFINITIONS

In the description and examples that follow, a number of terms are used herein. In order to provide a clear and consistent understanding of the specification and claims, including the scope to be given such terms, the following definitions are provided:

ADVANTAGE=It is the advantage the hybrid to be patented has compared to another hybrid for yield (bushels per acre), moisture (drier is an advantage), income, population, stand (plants not stalk lodging is an advantage), roots (plants not root lodging is an advantage), and test weight, respectively, in strip tests.

BAR PLT=BARREN PLANTS. This is the percent of plants per plot that were not barren (lack ears). 5 B/STK= BRITTLE STALKS RATING. This is a 1-9 rating where a 1, 5, and 9 represent serious, average, and little or no potential for brittle stalk breakage.

BRT STK=BRITTLE STALKS. This is a measure of the stalk breakage near the time of pollination, and is an indication of whether a hybrid would snap or break near the time of flowering under severe winds. Data are presented as percentage of plants that did not snap.

BU ACR=YIELD (BUSHELS/ACRE). Actual yield of the grain at harvest adjusted to 15.5% moisture. ABS is in absolute terms and % MN is percent of the mean for the experiments in which the hybrid was grown.

D/D=DRYDOWN. This represents the relative rate at which a hybrid will reach acceptable harvest moisture compared to other hybrids on a 1–9 rating scale. A high score indicates a hybrid that dries relatively fast while a low score indicates a hybrid that dries slowly.

D/E=DROPPED EARS RATING. This is a 1–9 rating where a 1, 5, and 9 represent serious, average, and little or no ear droppage potential, respectively.

DRP EAR=DROPPED EARS. This is a measure of the number of dropped ears per plot and represents the percentage of plants that did not drop ears prior to harvest.

D/T=DROUGHT TOLERANCE. This represents a 1–9 rating for drought tolerance, and is based on data obtained under stress conditions. A high score indicates good drought tolerance and a low score indicates poor drought tolerance.

E/HT=EAR HEIGHT RATING. This is a 1–9 rating with a 1, 5, and 9 representing a very low, average, and very high ear placement, respectively.

EAR HT=EAR HEIGHT. The ear height is a measure from the ground to the top developed ear node attachment and is measured in inches.

EST CNT=EARLY STAND COUNT. This is a measure of the stand establishment in the spring and represents the number of plants that emerge on a per plot basis for the hybrid.

GDU BL=GDU TO BLACKLAYER. This is the number of growing degree units required for the hybrid to reach blacklayer from the time that it was planted. Growing degree units are calculated by the Barger Method, where the heat units for a 24-hour period are:

$$GDU = \frac{(Max. + Min.)}{2} - 50$$

The highest maximum used is 86° F. and the lowest minimum used is 50° F. For each inbred or hybrid it takes a certain number of GDUs to reach various stages of plant development.

GDU SHD=GDU TO SHED. The number of growing degree units (GDUs) or heat units required for a hybrid to have approximately 50 percent of the plants shedding pollen and is measured from the time of planting.

GDU SLK=GDU TO SILK. The number of growing degree units required for a hybrid to have approximately 50 percent of the plants with silk emergence from time of planting.

GRN APP=G/A=GRAIN APPEARANCE. This is a 1 to 9 rating for the general quality of the shelled grain as it is harvested based on such factors as the color of the harvested grain, any mold on the grain, and any cracked grain. High scores indicate good grain quality and low scores indicate poor grain quality.

H/POP=YIELD AT HIGH DENSITY. Yield ability at relatively high plant densities on a 1–9 relative rating system with a higher number indicating the hybrid responds well to high plant densities for yield relative to other hybrids. A 1, 5, and 9 would represent very poor, average, and very good yield response, respectively, to increased plant density.

INCOME/ACRE: Relative income per acre assuming drying costs of two cents per point above 15.5 percent harvest moisture and market price of $2.25 per bushel.

L/POP=YIELD AT LOW DENSITY. Yield ability at relatively low plant densities on a 1–9 relative system with a higher number indicating the hybrid responds well to low plant densities for yield relative to other hybrids. -A 1, 5, and 9 would represent very poor, average, and very good yield response, respectively, to low plant density.

MST=MOIST=HARVEST MOISTURE. Harvest moisture is the actual percentage moisture of the grain at harvest.

MST RM=MOISTURE RM. This represents the Minnesota Relative Maturity Rating (MN RM) for the hybrid and is based on the harvest moisture of the grain relative to a standard set of checks of previously determined MN RM rating. Linear regression analysis is used to compute this rating.

P/HT=PLANT HEIGHT RATING. This is a 1–9 rating with a 1, 5, and 9 representing a very short, average, and very tall hybrid, respectively.

PLT HT=PLANT HEIGHT. This is a measure of the height of the plant from the ground to the tip of the tassel in inches.

PoP K/ACRE: Plants per 0.001 acre.

PERCENT WINS: For yield, moisture, income, populations, stand, roots, and test weight, it would be the percentage of comparisons that the hybrid to be patented yielded more, had lower harvest moisture percentage, had greater income per acre, had better stalks, had better roots, and had higher test weight, respectively, in strip tests.

R/L=ROOT LODGING RATING. A 1–9 rating where a higher score indicates less root lodging potential (1 is very poor, 5 is intermediate, and 9 is very good, respectively, for resistance to root lodging).

ROOT (%): Percentage of plants that did not root lodge (lean greater than 30 degrees from vertical) taken on strip test plots.

RT LDG=ROOT LODGING. Root lodging is the percentage of plants that do not root lodge; plants that lean from the vertical axis at an approximately 30° angle or greater would be counted as root lodged.

S/L=STALK LODGING RATING. This is a 1-9 rating where a higher score indicates less stalk lodging potential (1 is very poor, 5 is intermediate, and 9 is very good, respectively, for resistance to stalk lodging).

SDG VGR=S/VIG=SEEDLING VIGOR. This is the visual rating (1 to 9) of the amount of vegetative growth after emergence at the seedling stage (approximately five leaves). A higher score indicates better vigor and a low score indicates poorer vigor.

STA GRN=STGR=STAY GREEN. Stay green is the measure of plant health near the time of black layer formation (physiological maturity) using a 1–9 visual rating. A high score indicates better late-season plant health and a low score indicates poor plant health.

STAND (%): Percentage of plants that did not break (lodge) below the ear taken on strip test plots.

STK LDG=STALK LODGING. This is the percentage of plants that did not stalk lodge (stalk breakage) as measured by either natural lodging or pushing the stalks and determining the percentage of plants that break below the ear.

T/WT=TEST WEIGHT RATING. This is a 1–9 relative rating with a 1, 5, and 9 indicating very low, average, and very high test weight, respectively.

TST WTA=TEST WEIGHT. The measure of the weight of the grain in pounds for a given volume (bushel) adjusted for percent moisture.

YLD=YIELD FOR MATURITY. This represents a 1–9 rating for a hybrid's yield potential. 1, 5, and 9 would represent very poor, average, and very high yield potential, respectively, relative to other hybrids of a similar maturity.

DETAILED DESCRIPTION OF THE INVENTION

Pioneer Brand Hybrid 3394 is a single cross, yellow endosperm, dent corn hybrid with superior yield in its maturity. It has stable yield across environments, has above average grain appearance with average test weight, and has exceptional stay green. 3394 has excellent seedling vigor and very good drought tolerance. The inventor has observed that the leaf angle is semi upright and the leaf is short and wide, which is a unique characteristic of this hybrid. The hybrid has the potential to form an abscision layer and drop ears free from the husk.

This hybrid has the following characteristics based on the descriptive data collected primarily at Johnston, Iowa.

VARIETY DESCRIPTION INFORMATION
HYBRID = PIONEER BRAND 3394
Type: Dent    Region Best Adapted: Central Corn Belt

A. Maturity:

| | |
|---|---|
| Minnesota Relative Maturity Rating (harvest moisture): | 111 |
| GDU's to Physiological maturity (black layer): | 2760 |
| GDU's to 50% Silk: | 1442 |

$$\text{GDU's} = \frac{[\text{Max. Temp.} (<-86°\text{ F.}) + \text{Min. Temp} (>-50°\text{ F.})]^*}{2} - 50$$

B. Plant Characteristics:

| | |
|---|---|
| Plant height (to tassel tip): | 296 cm |
| Length of top ear internode: | 16 cm |
| Number of ears per stalk: | Single |
| Ear height (to base of top ear): | 101 cm |
| Number of tillers: | None |
| Cytoplasm type: | Normal |

C. Leaf:

| | |
|---|---|
| Color: | Dark Green (B14) |
| Angle from Stalk: | <30 degrees |
| Marginal Waves: | Few (WF9) |
| Number of Leaves (mature plants): | 20 |
| Sheath Pubescence: | Light (W22) |
| Longitudinal Creases: | Many (PA11) |
| Length (Ear node leaf): | 94 cm |
| Width (widest point, ear node leaf): | 10 cm |

D. Tassel:

| | |
|---|---|
| Number lateral branches: | 6 |
| Branch Angle from central spike: | >45 degrees |
| Pollen Shed: | Heavy (KY21) |
| Peduncle Length (top leaf to basal branches): | 22 cm |
| Anther Color: | Purple |
| Glume Color: | Green |

E. Ear (Husked Ear Data Except When Stated Otherwise):

| | |
|---|---|
| Length: | 20 cm |
| Weight: | 238 gm |
| Mid-point Diameter: | 47 mm |
| Silk Color: | Pink |
| Husk Extension (Harvest stage): | Short (Ears Exposed) |
| Husk Leaf: | Short (< 8 cm) |
| Taper of Ear: | Slight |
| Position of Shank (dry husks): | Upright |
| Kernel Rows: | Slightly Curved, Distinct Number = 16 |
| Husk Color (fresh): | Light Green |
| Husk Color (dry): | Buff |
| Shank Length: | 11 cm |
| Shank (No. of internodes): | 7 |

F. Kernel (Dried):

Size (from ear mid-point)

| | |
|---|---|
| Length: | 13 mm |
| Width: | 8 mm |
| Thick: | 4 mm |
| Shape Grade (% rounds): | <20% |
| Pericarp Color: | Colorless |
| Aleurone Color: | Homozygous Yellow |
| Endosperm Color: | Yellow |
| Endosperm Type: | Normal Starch |
| Gm Wt/100 Seeds (unsized): | 34 gm |

G. Cob:

| | |
|---|---|
| Diameter at mid-point: | 26 mm |
| Strength: | Strong |
| Color: | Red |

H. Diseases:

| | |
|---|---|
| Corn Lethal Necrosis (MCMV = Maize Chlorotic Mottle Virus and MDMV = Maize Dwarf Mosaic Virus): | Resistant |
| Common Smut (*U. maydis*): | Highly Resistant |
| Anthracnose Stalk Rot (*C. graminicola*): | Intermediate |
| S. Leaf Blight (*B. maydis*): | Intermediate |
| N. Leaf Blight (*E. turcicum*): | Intermediate |
| Gray Leaf Spot (*C. zeae*): | Susceptible |
| Goss's Wilt (*C. nebraskense*): | Highly Resistant |
| Head Smut (*S. reiliana*): | Highly Resistant |
| Fusarium Ear Mold (*F. moniliforme*): | Resistant |

I. Insects:

| | |
|---|---|
| European Corn Borer-1 Leaf Damage (Pre-flowering): | Susceptible |
| European Corn Borer-2 | Intermediate |

VARIETY DESCRIPTION INFORMATION
HYBRID = PIONEER BRAND 3394
Type: Dent   Region Best Adapted: Central Corn Belt (Post-flowering):
The above descriptions are based on a scale of 1–9, 1 being highly susceptible, 9 being highly resistant.

| | |
|---|---|
| S (Susceptible): | Would generally represent a score of 1–3. |
| I (Intermediate): | Would generally represent a score of 4–5. |
| R (Resistant): | Would generally represent a score of 6–7. |
| H (Highly Resistant): | Would generally represent a score of 8–9. Highly resistant does not imply the inbred is immune. |

J. Variety Most Closely Resembling:

| Character | Hybrid |
|---|---|
| Maturity | Pioneer Brand 3379 |
| Usage | Pioneer Brand 3379 |

*If maximum is greater than 86 degrees fahrenheit, then 86 is used and if minimum is less than 50, then 50 is used. Heat units accumulated daily and can not be less than 0.

Items B, C, D, E, F, and G are based on a maximum of two reps of data primarily from Johnston, Iowa in 1990.

This invention includes the hybrid corn seed of 3394, the hybrid corn plant produced from the hybrid corn seed, and variants, mutants, and modifications of 3394. This invention also relates to the use of 3394 in producing three-way and double cross hybrids.

The terms variant, trivial modification, and mutant refer to a hybrid seed where a plant produced by that hybrid seed which is phenotypically similar to 3394.

As used herein, the term "plant" includes plant cells, plant protoplast, plant cell or tissue culture from which corn plants can be regenerated, plant calli, plant clumps and plant cells that are intact in plants or parts of plants, such as flowers, kernels, ears, cobs, leaves, husks, stalks and the like.

Tissue culture of corn is described in European Patent Application, publication number 160,390, incorporated herein by reference. Corn tissue culture procedures are also described in Green and Rhodes, "Plant Regeneration in Tissue Culture of Maize," *Maize for Biological Research*, (Plant Molecular Biology Association, Charlottesville, Va. 1982) at 367–372 and in Duncan, et al., "The Production of Callus Capable of Plant Regeneration from Immature Embryos of Numerous Zea Mays Genotypes," 165 *Planta* 322–332 (1985).

USES OF CORN

Corn is used as human food, livestock feed, and as raw material in industry. The food uses of corn, in addition to human consumption of corn kernels, include both products of dry- and wet-milling industries. The principal products of corn dry milling are grits, meal and flour. The corn wet-milling industry can provide starch, syrups, and dextrose for food use. Corn oil is recovered from corn germ, which is a by-product of both dry- and wet-milling industries.

Corn is also used extensively as livestock feed primarily to beef cattle, dairy cattle, hogs, and poultry.

Industrial uses of corn are mainly from corn starch from the wet-milling industry and corn flour from the dry-milling industry. The industrial applications of corn starch and flour are based on functional properties, such as viscosity, film formation, adhesive properties, and ability to suspend particles. The corn starch and flour have application in the paper and textile industries. Other industrial uses include applications in adhesives, building materials, foundry binders, laundry starches, explosives, oil-well muds, and other mining applications.

Plant parts other than the grain of corn are also used in industry. Stalks and husks are made into paper and wallboard and cobs are used for fuel and to make charcoal.

The seed of 3394, the hybrid corn plant produced from the seed, and various parts of the hybrid corn plant can be utilized for human food, livestock feed, and as a raw material in industry.

EXAMPLE 1

Research Comparisons for Pioneer Hybrid 3394

Comparisons of the characteristics for Pioneer Brand Hybrid 3394 were made against Pioneer Brand Hybrids 3503, 3417, 3398, 3379, 3362, and 3241; Garst Brand Hybrid GR8532; and Wyffel Brand Hybrids WYF670 and WYF627. These hybrids are grown in the Central and Eastern Corn Belt and have similar maturity. Table 1A compares Pioneer Brand 3394 to Pioneer Brand 3503. 3394 has higher yield and grain harvest moisture, but lower test weight than 3503. 3394 is a taller hybrid with higher ear placement and flowers (GDU Shed) later than 3503. Compared to 3503, 3394 has poorer grain appearance, better stay green, better resistance to stalk lodging, but is more susceptible to root lodging and has fewer brittle stalks.

The results in Table 1B compare Pioneer Brand Hybrid 3394 to Pioneer Brand Hybrid 3417. 3394 has higher yield, grain harvest moisture, and test weight than 3417. 3394 is a taller hybrid, has higher ear placement, and flowers (GDU Shed) later than 3417. 3394 is better agronomically than 3417, having better grain appearance and stay green, better stalk lodging resistance and fewer brittle stalks, but is more susceptible to root lodging.

Table 1C results show Pioneer Brand Hybrid 3394 is higher yielding but has lower grain moisture and test weight than Pioneer Brand Hybrid 3398. 3394 has more barren plants, but has better seedling vigor and more plants are established early than 3398. 3394 is taller and has a higher ear placement compared to 3398. 3394 flowers (GDU Shed) later than 3398. 3394 has slightly poorer grain appearance and is more susceptible to root lodging, but has better stay green and more resistance to stalk lodging than 3398.

The results in Table 1D compare Pioneer Brand Hybrid 3394 to Pioneer Brand Hybrid 3379. 3394 outyields and has higher test weight but slightly lower grain moisture than 3379. 3394 and 3379 have similar early stand count, but 3394 has better seedling vigor. 3394 has better stay green and is more resistant to stalk and root lodging than 3379.

Table 1E, comparing Pioneer Brand Hybrid 3394 to Pioneer Brand Hybrid 3362, shows 3394 has higher yield, grain moisture, and test weight than 3362. 3394 is a taller hybrid, has higher ear placement, and sheds (GDU Shed) later than 3362. 3394 is more susceptible to root lodging, but has better stay green and stalk lodging resistance than 3362.

Table 1F compares Pioneer Brand 3394 to Pioneer Brand 3241. 3394 has higher yield and test weight and lower grain moisture than 3241. 3394 is shorter with lower ear placement and flowers (GDU Shed) slightly earlier than 3241. Compared to 3241, 3394 has poorer grain appearance, more susceptibility to stalk lodging, more resistance to root lodging, and fewer brittle stalks.

Table 1G results show Pioneer Brand Hybrid 3394 has higher grain yield but lower grain moisture and test weight than Garst Brand Hybrid GR8532. 3394 is significantly taller and has a higher ear placement than GR8532. 3394 flowers (GDU Shed) later than GR8532. 3394 has better stay green and stalk lodging resistance, but is more susceptible to root lodging than GR8532.

Table 1H compares Pioneer Brand Hybrid 3394 to Wyffels Brand Hybrid WYF670. 3394 significantly out-yields WYF670 but has similar test weight and lower grain moisture. 3394 is taller with higher ear placement and flowers (GDU Shed) later than WYF670. Agronomically, 3394 is better than WYF670, having better grain appearance, stay green, and stalk and root lodging resistance.

Table 1I, comparing Pioneer Brand Hybrid 3394 to Wyffels Brand Hybrid WYF627, shows 3394 is higher yielding, has higher test weight, but has lower grain moisture than WYF627. 3394 is a taller hybrid and has higher ear placement than WYF627. 3394 flowers (GDU Shed) later than WYF627. 3394 has significantly better stay green and stalk lodging resistance compared to WYF627.

TABLE 1A

VARIETY #1 - 3394
VARIETY #2 - 3503

| YEAR | VAR # | BU ACR ABS | BU ACR % MN | MST ABS | PLT HT ABS | EAR HT ABS | SDG VGR ABS | EST CNT ABS | DRP EAR ABS | GDU SHD ABS | TST WTA ABS | GRN APP ABS | STA GRN ABS | STK LDG ABS | RT LDG ABS | BRT STK ABS |
|---|---|---|---|---|---|---|---|---|---|---|---|---|---|---|---|---|
| 89 | 1 | 156.9 | 110 | 17.0 | 109.7 | 46.7 | 5.9 | 61.7 | 97.5 | 1345 | 59.2 | 6.2 | 5.3 | 89.9 | 94.4 | |
|  | 2 | 144.2 | 102 | 17.5 | 104.8 | 43.5 | 5.9 | 61.1 | 98.3 | 1310 | 61.2 | 5.8 | 5.6 | 83.1 | 98.3 | |
|  | LOCS | 9 | 9 | 9 | 3 | 3 | 4 | 7 | 5 | 3 | 9 | 9 | 4 | 7 | 5 | |
|  | PROB | .005# | .007# | .031+ | .041+ | .101 | .000# | .739 | .186 | .109 | .000# | .486 | .724 | .087* | .525 | |
| 90 | 1 | 163.1 | 111 | 20.6 | 98.2 | 45.6 | 7.0 | 60.4 | 99.5 | 1443 | 57.0 | 7.0 | 6.6 | 94.6 | 96.7 | 98.7 |
|  | 2 | 146.2 | 99 | 20.3 | 91.5 | 41.0 | 5.9 | 57.6 | 99.8 | 1375 | 58.7 | 7.6 | 4.4 | 90.9 | 97.6 | 97.5 |
|  | LOCS | 182 | 182 | 182 | 97 | 97 | 103 | 125 | 123 | 60 | 180 | 124 | 99 | 175 | 57 | 9 |
|  | PROB | .000# | .000# | .001# | .000# | .000# | .000# | .000# | .029+ | .000# | .000# | .000# | .000# | .000# | .461 | .086* |
| TOTAL SUM | 1 | 162.8 | 111 | 20.4 | 98.5 | 45.7 | 6.9 | 60.5 | 99.4 | 1438 | 57.1 | 7.0 | 6.6 | 94.4 | 96.5 | 98.7 |
|  | 2 | 146.1 | 100 | 20.1 | 91.9 | 41.1 | 5.9 | 57.7 | 99.7 | 1372 | 58.8 | 7.4 | 4.4 | 90.6 | 97.7 | 97.5 |
|  | LOCS | 191 | 191 | 191 | 100 | 100 | 107 | 132 | 128 | 63 | 189 | 133 | 103 | 182 | 62 | 9 |
|  | DIFF | 16.7 | 11 | 0.3 | 6.7 | 4.6 | 1.0 | 2.7 | 0.3 | 66 | 1.8 | 0.5 | 2.2 | 3.8 | 1.2 | 1.2 |
|  | PROB | .000# | .000# | .004# | .000# | .000# | .000# | .000# | .016+ | .000# | .000# | .000# | .000# | .000# | .345 | .086* |

* = 10% SIG
+ = 5% SIG
# = 1% SIG

TABLE 1B

VARIETY #1 - 3394
VARIETY #2 - 3417

| YEAR | VAR # | BU ACR ABS | BU ACR % MN | MST ABS | PLT HT ABS | EAR HT ABS | SDG VGR ABS | EST CNT ABS | DRP EAR ABS | GDU SHD ABS | TST WTA ABS | GRN APP ABS | STA GRN ABS | STK LDG ABS | RT LDG ABS | BRT STK ABS |
|---|---|---|---|---|---|---|---|---|---|---|---|---|---|---|---|---|
| 89 | 1 | 159.7 | 109 | 18.2 | 106.6 | 48.6 | 5.8 | 60.9 | 98.5 | 1353 | 58.5 | 6.3 | 5.3 | 92.0 | 96.2 | 97.0 |
|  | 2 | 154.0 | 105 | 17.9 | 103.4 | 41.6 | 5.8 | 61.2 | 99.2 | 1308 | 57.7 | 5.7 | 4.1 | 81.2 | 93.6 | 98.9 |
|  | LOCS | 18 | 18 | 18 | 8 | 8 | 6 | 12 | 9 | 6 | 18 | 18 | 7 | 15 | 9 | 1 |
|  | PROB | .174 | .181 | .209 | .011+ | .000# | .862 | .637 | .300 | .003# | .021+ | .133 | .047+ | .009# | .124 | |
| 90 | 1 | 164.3 | 110 | 20.3 | 98.6 | 45.4 | 7.0 | 60.7 | 99.6 | 1448 | 57.0 | 7.2 | 6.3 | 95.1 | 96.6 | 97.8 |
|  | 2 | 147.7 | 99 | 19.6 | 94.8 | 37.8 | 5.8 | 59.0 | 99.8 | 1392 | 56.8 | 6.9 | 4.5 | 92.1 | 99.0 | 93.9 |
|  | LOCS | 252 | 252 | 253 | 130 | 130 | 131 | 166 | 161 | 68 | 250 | 161 | 134 | 250 | 80 | 15 |
|  | PROB | .000# | .000# | .000# | .000# | .000# | .000# | .000# | .028+ | .000# | .000# | .009# | .000# | .000# | .002# | .095* |
| TOTAL SUM | 1 | 164.0 | 110 | 20.2 | 99.0 | 45.6 | 7.0 | 60.7 | 99.5 | 1440 | 57.1 | 7.1 | 6.3 | 94.9 | 96.6 | 97.7 |
|  | 2 | 148.1 | 99 | 19.5 | 95.3 | 38.0 | 5.8 | 59.2 | 99.7 | 1385 | 56.8 | 6.8 | 4.5 | 91.4 | 98.4 | 94.2 |
|  | LOCS | 270 | 270 | 271 | 138 | 138 | 137 | 178 | 170 | 74 | 268 | 179 | 141 | 265 | 89 | 16 |
|  | DIFF | 15.8 | 10 | 0.7 | 3.7 | 7.6 | 1.2 | 1.5 | 0.2 | 55 | 0.3 | 0.3 | 1.8 | 3.5 | 1.9 | 3.5 |
|  | PROB | .000# | .000# | .000# | .000# | .000# | .000# | .000# | .014+ | .000# | .000# | .003# | .000# | .000# | .009# | .108 |

* = 10% SIG
+ = 5% SIG
# = 1% SIG

TABLE 1C

VARIETY #1 - 3394
VARIETY #2 - 3398

| VAR | BU ACR | BU ACR | MST | BAR PLT | PLT HT | EAR HT | SDG VGR | EST CNT | DRP EAR |

TABLE 1C-continued

| YEAR | # | ABS | % MN ABS | ABS | ABS | ABS | ABS | ABS | ABS |
|---|---|---|---|---|---|---|---|---|---|
| 88 | 1 | 105.1 | 115 | 19.3 | 90.9 | 95.0 | 41.5 | 5.8 | 53.5 | 100.0 |
|  | 2 | 97.2 | 106 | 21.3 | 95.5 | 87.8 | 34.3 | 5.8 | 60.3 | 100.0 |
|  | LOCS | 2 | 2 | 2 | 2 | 2 | 2 | 3 | 2 | 2 |
|  | PROB | .499 | .499 | .097* | .156 | .109 | .022+ | .000# | .476 | 1.00 |
| 89 | 1 | 172.3 | 111 | 19.4 |  | 101.0 | 48.5 | 6.3 | 58.5 | 99.7 |
|  | 2 | 152.4 | 98 | 20.2 |  | 101.7 | 41.0 | 6.3 | 58.4 | 100.0 |
|  | LOCS | 8 | 8 | 8 |  | 3 | 3 | 3 | 5 | 4 |
|  | PROB | .005# | .007# | .056* |  | .881 | .013+ | 1.00 | .960 | .391 |
| 90 | 1 | 165.0 | 109 | 20.5 |  | 100.7 | 44.1 | 7.1 | 61.3 | 99.6 |
|  | 2 | 155.1 | 102 | 20.9 |  | 94.4 | 38.8 | 5.8 | 59.1 | 99.8 |
|  | LOCS | 94 | 94 | 95 |  | 40 | 40 | 40 | 64 | 67 |
|  | PROB | .000# | .000# | .003# |  | .000# | .000# | .000# | .000# | .119 |
| TOTAL SUM | 1 | 164.4 | 109 | 20.4 | 90.9 | 100.4 | 44.3 | 7.0 | 60.9 | 99.7 |
|  | 2 | 153.8 | 102 | 20.9 | 95.5 | 94.6 | 38.7 | 5.9 | 59.0 | 99.8 |
|  | LOCS | 104 | 104 | 105 | 2 | 45 | 45 | 46 | 71 | 73 |
|  | DIFF | 10.6 | 7 | 0.5 | 4.5 | 5.9 | 5.5 | 1.1 | 1.9 | 0.2 |
|  | PROB | .000# | .000# | .000# | .156 | .000# | .000# | .000# | .000# | .090* |

| YEAR | VAR # | GDU SHD ABS | TST WTA ABS | GRN APP ABS | STA GRN ABS | STK LDG ABS | RT LDG ABS | BRT STK ABS |
|---|---|---|---|---|---|---|---|---|
| 88 | 1 | 1453 | 57.5 | 7.3 | 5.2 | 99.4 | 98.3 |  |
|  | 2 | 1413 | 56.4 | 6.3 | 3.8 | 98.3 | 100.0 |  |
|  | LOCS | 2 | 2 | 2 | 3 | 2 | 2 |  |
|  | PROB | .156 | .296 | .000# | .094* | .500 | .500 |  |
| 89 | 1 | 1415 | 57.5 | 6.3 | 5.5 | 91.4 | 98.8 | 97.0 |
|  | 2 | 1357 | 57.3 | 6.3 | 5.0 | 77.3 | 97.0 | 98.9 |
|  | LOCS | 3 | 8 | 8 | 3 | 7 | 5 | 1 |
|  | PROB | .075* | .714 | .000# | .729 | .046+ | .303 |  |
| 90 | 1 | 1428 | 57.1 | 6.7 | 6.3 | 95.5 | 95.4 | 96.8 |
|  | 2 | 1369 | 57.3 | 7.0 | 4.1 | 92.0 | 98.2 | 95.3 |
|  | LOCS | 21 | 95 | 43 | 52 | 88 | 34 | 9 |
|  | PROB | .000# | .013+ | .085* | .000# | .003# | .062* | .414 |
| TOTAL SUM | 1 | 1428 | 57.11 | 6.6 | 6.2 | 95.3 | 95.9 | 96.9 |
|  | 2 | 1371 | 57.3 | 6.8 | 4.1 | 91.0 | 98.2 | 95.7 |
|  | LOCS | 26 | 105 | 53 | 58 | 97 | 41 | 10 |
|  | DIFF | 57 | 0.2 | 0.2 | 2.0 | 4.2 | 2.2 | 1.2 |
|  | PROB | .000# | .055* | .163 | .000# | .000# | .085* | .484 |

\* = 10% SIG
+ = 5% SIG
# = 1% SIG

TABLE 1D

VARIETY #1 - 3394
VARIETY #2 - 3379

| YEAR | VAR # | BU ACR ABS | BU ACR % MN | MST ABS | BAR PLT ABS | PLT HT ABS | EAR HT ABS | SDG VGR ABS | EST CNT ABS | DRP EAR ABS |
|---|---|---|---|---|---|---|---|---|---|---|
| 88 | 1 | 125.7 | 110 | 20.4 | 91.4 | 89.6 | 39.4 | 6.2 | 59.6 | 99.9 |
|  | 2 | 116.3 | 102 | 22.3 | 90.9 | 88.8 | 37.9 | 5.9 | 64.4 | 99.9 |
|  | LOCS | 16 | 16 | 16 | 5 | 9 | 9 | 10 | 9 | 13 |
|  | PROB | .050* | .075* | .001# | .803 | .761 | .273 | .440 | .009# | .700 |
| 89 | 1 | 162.8 | 108 | 20.1 |  | 109.9 | 50.8 | 6.6 | 59.7 | 98.8 |
|  | 2 | 154.2 | 102 | 19.8 |  | 111.1 | 50.4 | 5.5 | 60.1 | 99.5 |
|  | LOCS | 43 | 43 | 43 |  | 18 | 18 | 16 | 28 | 22 |
|  | PROB | .000# | .000# | .064* |  | .261 | .469 | .000# | .598 | .141 |
| 90 | 1 | 164.6 | 109 | 20.1 |  | 100.2 | 45.7 | 7.0 | 59.5 | 99.6 |
|  | 2 | 150.2 | 100 | 20.2 |  | 100.8 | 45.1 | 5.9 | 59.4 | 99.7 |
|  | LOCS | 271 | 271 | 272 |  | 143 | 143 | 141 | 173 | 145 |
|  | PROB | .000# | .000# | .236 |  | .054* | .036+ | .000# | .669 | .340 |
| TOTAL SUM | 1 | 162.5 | 109 | 20.1 | 91.4 | 100.6 | 45.9 | 6.9 | 59.5 | 99.5 |
|  | 2 | 149.1 | 100 | 20.3 | 90.9 | 101.2 | 45.3 | 5.8 | 59.7 | 99.7 |
|  | LOCS | 330 | 330 | 331 | 5 | 170 | 170 | 167 | 210 | 180 |
|  | DIFF | 13.4 | 9 | 0.2 | 0.5 | 0.6 | 0.6 | 1.1 | 0.2 | 0.1 |
|  | PROB | .000# | .000# | .110 | .803 | .054* | .015+ | .000# | .507 | .102 |

| YEAR | VAR # | GDU SHD ABS | TST WTA ABS | GRN APP ABS | STA GRN ABS | STK LDG ABS | RT LDG ABS | BRT STK ABS |
|---|---|---|---|---|---|---|---|---|
| 88 | 1 | 1441 | 57.3 | 8.0 | 4.9 | 94.3 | 96.2 | 100.0 |

TABLE 1D-continued

|  | | | | | | | | |
|---|---|---|---|---|---|---|---|---|
|  | 2 | 1444 | 56.5 | 7.6 | 5.2 | 90.3 | 70.5 | 100.0 |
|  | LOCS | 5 | 16 | 13 | 9 | 15 | 5 | 1 |
|  | PROB | .872 | .001# | .213 | .665 | .234 | .231 |  |
| 89 | 1 | 1364 | 57.3 | 6.1 | 6.0 | 92.4 | 97.2 | 98.0 |
|  | 2 | 1353 | 56.6 | 6.4 | 5.0 | 91.6 | 92.6 | 99.5 |
|  | LOCS | 14 | 43 | 38 | 14 | 36 | 17 | 2 |
|  | PROB | .086* | .000# | .249 | .075* | .557 | .056* | .166 |
| 90 | 1 | 1438 | 57.0 | 7.3 | 6.1 | 94.5 | 96.5 | 97.7 |
|  | 2 | 1434 | 57.0 | 7.2 | 5.1 | 94.3 | 95.5 | 96.5 |
|  | LOCS | 76 | 267 | 180 | 159 | 258 | 69 | 16 |
|  | PROB | .171 | .735 | .758 | .000# | .724 | .141 | .216 |
| TOTAL SUM | 1 | 1427 | 57.1 | 7.1 | 6.0 | 94.3 | 96.6 | 97.8 |
|  | 2 | 1423 | 56.9 | 7.1 | 5.1 | 93.8 | 93.6 | 97.0 |
|  | LOCS | 95 | 326 | 231 | 182 | 309 | 91 | 19 |
|  | DIFF | 04 | 0.1 | 0.0 | 0.0 | 0.4 | 3.0 | 0.8 |
|  | PROB | .076* | .008# | .948 | .000# | .370 | .018+ | .304 |

* = 10% SIG
+ = 5% SIG
# = 1% SIG

TABLE 1E

VARIETY #1 - 3394
VARIETY #2 - 3362

| YEAR | VAR # | BU ACR ABS | BU ACR % MN | MST ABS | PLT HT ABS | EAR HT ABS | SDG VGR ABS | EST CNT ABS | DRP EAR ABS | GDU SHD ABS | TST WTA ABS | GRN APP ABS | STA GRN ABS | STK LDG ABS | RT LDG ABS | BRT STK ABS |
|---|---|---|---|---|---|---|---|---|---|---|---|---|---|---|---|---|
| 89 | 1 | 164.1 | 109 | 19.9 | 103.9 | 50.5 | 6.6 | 59.4 | 99.0 | 1369 | 57.3 | 6.6 | 6.2 | 90.6 | 95.3 | 97.0 |
|  | 2 | 149.4 | 100 | 19.8 | 102.4 | 47.3 | 5.0 | 57.3 | 98.8 | 1336 | 56.9 | 6.0 | 3.8 | 80.2 | 94.6 | 99.1 |
|  | LOCS | 21 | 21 | 21 | 8 | 8 | 7 | 12 | 14 | 8 | 21 | 16 | 5 | 20 | 9 | 1 |
|  | PROB | .007# | .009# | .786 | .251 | .091* | .016+ | .200 | .543 | .006# | .012+ | .250 | .054* | .005# | .503 |  |
| 90 | 1 | 162.8 | 110 | 20.1 | 98.1 | 44.8 | 7.0 | 60.6 | 99.5 | 1446 | 57.2 | 7.1 | 6.3 | 94.9 | 96.4 | 97.8 |
|  | 2 | 143.7 | 98 | 19.7 | 95.0 | 41.6 | 5.5 | 58.2 | 99.7 | 1413 | 56.5 | 7.0 | 4.4 | 91.3 | 97.9 | 97.1 |
|  | LOCS | 221 | 221 | 222 | 115 | 115 | 121 | 148 | 139 | 70 | 220 | 130 | 121 | 212 | 77 | 17 |
|  | PROB | .000# | .000# | .001# | .000# | .000# | .000# | .000# | .007* | .000# | .000# | .676 | .000# | .000# | .012+ | .472 |
| TOTAL SUM | 1 | 162.9 | 110 | 20.1 | 98.5 | 45.2 | 6.9 | 60.5 | 99.5 | 1438 | 57.2 | 7.0 | 6.3 | 94.5 | 96.3 | 97.8 |
|  | 2 | 144.2 | 98 | 19.7 | 95.5 | 42.0 | 5.5 | 58.2 | 99.6 | 1405 | 56.5 | 6.9 | 4.4 | 90.3 | 97.6 | 97.2 |
|  | LOCS | 242 | 242 | 243 | 123 | 123 | 128 | 160 | 153 | 78 | 241 | 146 | 126 | 232 | 86 | 18 |
|  | DIFF | 18.8 | 12 | 0.4 | 3.0 | 3.2 | 1.4 | 2.4 | 0.2 | 33 | 0.6 | 0.1 | 1.9 | 4.2 | 1.3 | 0.6 |
|  | PROB | .000# | .000# | .001# | .000# | .000# | .000# | .000# | .109 | .000# | .000# | .366 | .000# | .000# | .020+ | .548 |

* = 10% SIG
+ = 5% SIG
# = 1% SIG

TABLE 1F

VARIETY #1 - 3394
VARIETY #2 - 3241

| YEAR | VAR # | BU ACR ABS | BU ACR % MN | MST ABS | PLT HT ABS | EAR HT ABS | SDG VGR ABS | EST CNT ABS | DRP EAR ABS | GDU SHD ABS | TST WTA ABS | GRN APP ABS | STA GRN ABS | STK LDG ABS | RT LDG ABS | BRT STK ABS |
|---|---|---|---|---|---|---|---|---|---|---|---|---|---|---|---|---|
| 88 | 1 | 136.5 | 109 | 20.8 | 70.5 | 34.5 | 5.0 |  | 100.0 |  | 57.4 | 8.3 | 6.0 | 92.6 | 93.4 |  |
|  | 2 | 146.5 | 118 | 23.2 | 79.5 | 39.0 | 6.0 |  | 100.0 |  | 56.3 | 7.8 | 4.0 |  | 97.4 | 46.2 |
|  | LOCS | 6 | 6 | 6 | 2 | 2 | 1 |  | 5 |  |  |  |  |  |  |  |
|  | PROB | .466 | .441 | .016+ | .205 | .205 |  |  | 1.00 |  | .137 | .580 |  | .207 | .456 |  |
| 89 | 1 | 173.8 | 107 | 24.2 | 110.0 | 54.0 | 7.5 | 57.4 | 99.7 | 1418 | 55.1 | 5.8 | 6.7 | 92.5 | 98.0 | 98.9 |
|  | 2 | 171.1 | 105 | 25.3 | 115.3 | 57.3 | 6.9 | 57.1 | 100.0 | 1398 | 55.0 | 7.1 | 6.8 | 96.2 | 90.4 | 97.8 |
|  | LOCS | 15 | 15 | 15 | 6 | 6 | 4 | 9 | 7 | 5 | 15 | 15 | 6 | 14 | 7 | 1 |
|  | PROB | .508 | .532 | .000# | .099* | .063* | .239 | .891 | .173 | .247 | .634 | .001# | .856 | .058* | .169 |  |
| 90 | 1 | 170.0 | 109 | 21.7 | 101.4 | 47.8 | 7.2 | 57.0 | 99.8 | 1428 | 56.2 | 7.1 | 6.2 | 94.2 | 99.4 |  |
|  | 2 | 164.2 | 105 | 23.9 | 107.4 | 50.3 | 7.0 | 56.8 | 99.7 | 1441 | 55.7 | 7.6 | 6.4 | 95.1 | 97.0 |  |
|  | LOCS | 93 | 93 | 93 | 47 | 47 | 38 | 57 | 51 | 24 | 91 | 82 | 62 | 90 | 10 |  |
|  | PROB | .000# | .000# | .000# | .000# | .000# | .168 | .682 | .385 | .015+ | .000# | .000# | .260 | .352 | .073* |  |
| TOTAL SUM | 1 | 168.7 | 109 | 22.0 | 101.2 | 48.0 | 7.2 | 57.1 | 99.8 | 1426 | 56.1 | 7.0 | 6.2 | 93.9 | 98.3 | 98.9 |
|  | 2 | 164.1 | 106 | 24.0 | 107.2 | 50.7 | 7.0 | 56.8 | 99.8 | 1433 | 55.6 | 7.5 | 6.4 | 95.4 | 89.2 | 97.8 |
|  | LOCS | 114 | 114 | 114 | 55 | 55 | 43 | 66 | 63 | 29 | 112 | 103 | 69 | 109 | 19 | 1 |

TABLE 1F-continued

VARIETY #1 - 3394
VARIETY #2 - 3241

|  |  |  |  |  |  |  |  |  |  |  |  |  |  |  |  |
|---|---|---|---|---|---|---|---|---|---|---|---|---|---|---|---|
| DIFF | 4.6 | 3 | 2.0 | 6.1 | 2.7 | 0.3 | 0.2 | 0.1 | 08 | 0.5 | 0.5 | 0.2 | 1.4 | 9.1 | 1.1 |
| PROB | .002# | .004# | .000# | .000# | .000# | .127 | .675 | .556 | .165 | .000# | .000# | .340 | .083* | .075* | |

\* = 10% SIG
\+ = 5% SIG
\# = 1% SIG

TABLE 1G

VARIETY #1 - 3394
VARIETY #2 - GR8532

| YEAR | VAR # | BU ACR ABS | BU ACR % MN | MST ABS | PLT HT ABS | EAR HT ABS | SDG VGR ABS | EST CNT ABS | DRP EAR ABS | GDU SHD ABS | TST WTA ABS | GRN APP ABS | STA GRN ABS | STK LDG ABS | RT LDG ABS | BRT STK ABS |
|---|---|---|---|---|---|---|---|---|---|---|---|---|---|---|---|---|
| 90 | 1 | 162.5 | 110 | 19.5 | 94.4 | 46.1 | 6.7 | 61.7 | 99.5 | 1445 | 57.2 | 7.2 | 6.2 | 93.2 | 96.5 | 99.1 |
|  | 2 | 137.1 | 93 | 20.9 | 83.4 | 37.9 | 5.6 | 60.7 | 99.8 | 1347 | 57.5 | 7.3 | 4.1 | 89.3 | 98.3 | 99.1 |
|  | LOCS | 94 | 94 | 94 | 55 | 55 | 67 | 70 | 64 | 32 | 92 | 63 | 56 | 92 | 34 | 7 |
|  | PROB | .000# | .000# | .000# | .000# | .000# | .000# | .044+ | .064* | .000# | .008# | .572 | .000# | .001# | .131 | .961 |
| TOTAL | 1 | 162.5 | 110 | 19.5 | 94.4 | 46.1 | 6.7 | 61.7 | 99.5 | 1445 | 57.2 | 7.2 | 6.2 | 93.2 | 96.5 | 99.1 |
| SUM | 2 | 137.1 | 93 | 20.9 | 83.4 | 37.9 | 5.6 | 60.7 | 99.8 | 1347 | 57.5 | 7.3 | 4.1 | 89.3 | 98.3 | 99.1 |
|  | LOCS | 94 | 94 | 94 | 55 | 55 | 67 | 70 | 64 | 32 | 92 | 63 | 56 | 92 | 34 | 7 |
|  | DIFF | 25.4 | 17 | 1.4 | 11.1 | 8.2 | 1.1 | 1.1 | 0.3 | 98 | 0.3 | 0.1 | 2.1 | 3.8 | 1.8 | 0.0 |
|  | PROB | .000# | .000# | .000# | .000# | .000# | .000# | .044+ | .064* | .000# | .008# | .572 | .000# | .001# | .131 | .961 |

\* = 10% SIG
\+ = 5% SIG
\# = 1% SIG

TABLE 1H

VARIETY #1 - 3394
VARIETY #2 - WYF670

| YEAR | VAR # | BU ACR ABS | BU ACR % MN | MST ABS | BAR PLT ABS | PLT HT ABS | EAR HT ABS | SDG VGR ABS | EST CNT ABS | DRP EAR ABS |
|---|---|---|---|---|---|---|---|---|---|---|
| 88 | 1 | 108.7 | 113 | 20.4 | 90.4 | 94.3 | 41.7 | 5.6 | 58.6 | 99.6 |
|  | 2 | 94.9 | 99 | 22.9 | 94.0 | 83.5 | 32.7 | 5.6 | 61.8 | 100.0 |
|  | LOCS | 5 | 5 | 5 | 3 | 3 | 3 | 4 | 4 | 3 |
|  | PROB | .010+ | .004# | .025+ | .163 | .000# | .102 | .000# | .375 | .423 |
| 89 | 1 | 155.5 | 107 | 18.3 |  | 110.2 | 50.5 | 6.4 | 61.4 | 98.4 |
|  | 2 | 137.2 | 94 | 20.2 |  | 98.9 | 41.4 | 6.2 | 60.3 | 99.9 |
|  | LOCS | 20 | 20 | 20 |  | 9 | 9 | 7 | 12 | 14 |
|  | PROB | .000# | .000# | .000# |  | .000# | .000# | .766 | .274 | .005# |
| 98 | 1 | 163.2 | 110 | 20.0 |  | 102.0 | 45.2 | 7.1 | 59.4 | 99.5 |
|  | 2 | 139.3 | 94 | 20.9 |  | 90.5 | 36.8 | 5.9 | 58.2 | 99.8 |
|  | LOCS | 119 | 119 | 119 |  | 64 | 64 | 70 | 83 | 60 |
|  | PROB | .000# | .000# | .000# |  | .000# | .000# | .000# | .010+ | .056* |
| TOTAL SUM | 1 | 160.2 | 110 | 19.8 | 90.4 | 102.7 | 45.7 | 6.9 | 59.6 | 99.3 |
|  | 2 | 137.5 | 94 | 20.9 | 94.0 | 91.2 | 37.2 | 5.9 | 58.6 | 99.9 |
|  | LOCS | 144 | 144 | 144 | 3 | 76 | 76 | 81 | 99 | 77 |
|  | DIFF | 22.7 | 16 | 1.1 | 3.6 | 11.5 | 8.5 | 1.1 | 1.0 | 0.5 |
|  | PROB | .000# | .000# | .000# | .163 | .000# | .000# | .000# | .018+ | .001# |

| YEAR | VAR # | GDU SHD ABS | TST WTA ABS | GRN APP ABS | STA GRN ABS | STK LDG ABS | RT LDG ABS | BRT STK ABS |
|---|---|---|---|---|---|---|---|---|
| 88 | 1 | 1432 | 57.2 | 7.3 | 4.5 | 98.6 | 98.1 |  |
|  | 2 | 1355 | 55.5 | 6.0 | 5.1 | 99.3 | 100.0 |  |
|  | LOCS | 3 | 5 | 5 | 4 | 5 | 3 |  |
|  | PROB | .175 | .002# | .019+ | .703 | .430 | .196 |  |
| 89 | 1 | 1317 | 58.5 | 6.4 | 5.6 | 92.6 | 95.8 | 97.0 |
|  | 2 | 1254 | 58.6 | 5.9 | 4.3 | 84.1 | 92.7 | 100.0 |
|  | LOCS | 5 | 20 | 20 | 5 | 15 | 8 | 1 |
|  | PROB | .007# | .587 | .102 | .019+ | .018+ | .303 |  |
| 90 | 1 | 1448 | 57.3 | 7.2 | 6.2 | 95.0 | 96.6 | 99.2 |
|  | 2 | 1371 | 57.5 | 6.9 | 4.1 | 91.2 | 95.5 | 99.3 |
|  | LOCS | 39 | 118 | 80 | 71 | 109 | 30 | 7 |

TABLE 1H-continued

|  | PROB | .000# | .049+ | .011+ | .000# | .000# | .384 | .821 |
|---|---|---|---|---|---|---|---|---|
| TOTAL SUM | 1 | 1433 | 57.4 | 7.1 | 6.1 | 94.9 | 96.5 | 98.9 |
|  | 2 | 1357 | 57.6 | 6.6 | 4.1 | 90.7 | 95.3 | 99.4 |
|  | LOCS | 47 | 143 | 105 | 80 | 129 | 41 | 8 |
|  | DIFF | 76 | 0.1 | 0.4 | 2.0 | 4.2 | 1.3 | 0.5 |
|  | PROB | .000# | .187 | .001# | .000# | .000# | .242 | .447 |

\* = 10% SIG  
+ = 5% SIG  
# = 1% SIG

TABLE 1I

VARIETY #1 - 3394  
VARIETY #2 - WYF627

| YEAR | VAR # | BU ACR ABS | BU ACR % MN | MST ABS | PLT HT ABS | EAR HT ABS | SDG VGR ABS | EST CNT ABS | DRP EAR ABS | GDU SHD ABS | TST WTA ABS | GRN APP ABS | STA GRN ABS | STK LDG ABS | RT LDG ABS | BRT STK ABS |
|---|---|---|---|---|---|---|---|---|---|---|---|---|---|---|---|---|
| 89 | 1 | 146.7 | 104 | 17.8 | 125.0 | 53.8 | 7.2 | 62.5 | 98.2 | 1280 | 58.9 | 6.3 |  | 98.0 | 100.0 |  |
|  | 2 | 129.9 | 91 | 18.3 | 116.8 | 50.5 | 7.0 | 59.2 | 99.0 | 1230 | 58.5 | 6.3 |  | 96.0 | 100.0 |  |
|  | LOCS | 5 | 5 | 5 | 2 | 2 | 3 | 3 | 1 |  | 5 | 5 |  | 2 | 1 |  |
|  | PROB | .019+ | .032+ | .100 | .170 | .234 | .742 | .063* | .341 |  | .451 | .000# |  | .291 |  |  |
| 90 | 1 | 157.8 | 110 | 21.9 | 101.1 | 46.0 | 6.8 | 56.8 | 99.5 | 1446 | 56.2 | 7.1 | 6.4 | 94.9 | 97.2 | 100.0 |
|  | 2 | 143.0 | 99 | 22.3 | 98.1 | 43.9 | 6.0 | 57.5 | 99.6 | 1427 | 55.5 | 6.8 | 3.5 | 87.1 | 97.0 | 100.0 |
|  | LOCS | 57 | 57 | 57 | 23 | 23 | 26 | 32 | 36 | 14 | 57 | 35 | 26 | 57 | 17 | 2 |
|  | PROB | .000# | .000# | .073* | .003# | .002# | .008# | .443 | .563 | .017+ | .000# | .270 | .000# | .000# | .610 | 1.00 |
| TOTAL SUM | 1 | 156.9 | 110 | 21.6 | 103.0 | 46.6 | 6.8 | 57.3 | 99.3 | 1435 | 56.4 | 7.0 | 6.4 | 95.0 | 97.4 | 100.0 |
|  | 2 | 141.6 | 99 | 21.9 | 99.6 | 44.4 | 6.1 | 57.6 | 99.5 | 1414 | 55.8 | 6.8 | 3.5 | 87.4 | 97.1 | 100.0 |
|  | LOCS | 62 | 62 | 62 | 25 | 25 | 29 | 35 | 41 | 15 | 62 | 40 | 26 | 59 | 18 | 2 |
|  | DIFF | 15.0 | 11 | 0.4 | 3.4 | 2.2 | 0.7 | 0.3 | 0.2 | 21 | 0.6 | 0.2 | 2.9 | 7.5 | 0.3 | 0.0 |
|  | PROB | .000# | .000# | .048+ | .001# | .001# | .007# | .683 | .343 | .008# | .000# | .287 | .000# | .000# | .609 | 1.00 |

\* = 10% SIG  
+ = 5% SIG  
# = 1% SIG

EXAMPLE 2

Strip Test Data for Hybrid 3394

Comparison data was collected from strip tests that were grown by farmers. Each hybrid was grown in strips of 4, 6, 8, 12, etc. rows in fields depending on the size of the planter used. The data was collected from strip tests that had the hybrids in the same area and weighed. The moisture percentage was determined and bushels per acre was adjusted to 15.5 percent moisture. The number of comparisons represent the number of locations or replications for the two hybrids that were grown in the same field in close proximity and compared.

Comparison strip testing was done between Pioneer Brand Hybrid 3394 and Pioneer Brand Hybrids 3503, 3417, 3398, 3379, 3362, and 3241; Garst Brand Hybrid 8532; and Wyffels Brand Hybrid WYF670. The comparisons came from all the hybrid's adapted growing areas in the United States.

These results are presented in Table 2. The results show Pioneer Brand Hybrid 3394 had a yield advantage over compared hybrids except Pioneer Hybrid 3398 where it had a disadvantage of 2.8 bushels per acre. 3394 had a slight moisture disadvantage against Pioneer Hybrids 3503, 3417, and 3362, and Garst Hybrid 8532. 3394 showed a greater income advantage to the farmer based on adjusted gross income over all hybrids compared except Pioneer Hybrid 3398 where the disadvantage was $4.18 per acre. With the exception of Pioneer Hybrid 3398, 3394's yield and income advantage plus its advantage for other characteristics over these hybrids will make it an important addition for most of the areas where these hybrids are grown.

TABLE 2

PIONEER HYBRID 3394 VS PIONEER HYBRIDS 3503, 3417, 3398, 3379, 3362, AND 3241; GARST HYBRID GR8532; AND WYFFELS WYF670 FROM 1990 STRIP TESTS

| Brand | Product | Yield | Moist | Income/ Acre | Pop K/Acre | Stand (%) | Roots (%) | Test Wt |
|---|---|---|---|---|---|---|---|---|
| PIONEER | 3394 | 167.8 | 19.4 | 402.22 | 23.2 | 92 | 98 | 56.7 |
| PIONEER | 3503 | 154.6 | 19.1 | 371.57 | 22.9 | 87 | 96 | 58.5 |
| Advantage | | 13.2 | −0.3 | 30.65 | 0.3 | 5 | 2 | −1.8 |
| Number of Comparisons | | 159 | 159 | 159 | 85 | 68 | 40 | 133 |
| Percent Wins | | 87 | 40 | 83 | 54 | 45 | 5 | 6 |
| Probability of Difference | | 99 | 99 | 99 | 85 | 99 | 65 | 99 |
| PIONEER | 3394 | 169.3 | 19.4 | 405.74 | 23.6 | 91 | 98 | 56.7 |
| PIONEER | 3417 | 160.1 | 18.8 | 385.83 | 23.4 | 88 | 98 | 56.3 |
| Advantage | | 9.2 | −0.6 | 19.91 | 0.2 | 3 | 0 | 0.4 |
| Number of Comparisons | | 245 | 245 | 245 | 145 | 116 | 87 | 200 |
| Percent Wins | | 75 | 28 | 72 | 46 | 55 | 5 | 56 |
| Probability of Difference | | 99 | 99 | 99 | 84 | 99 | 2 | 99 |
| PIONEER | 3394 | 162.6 | 17.7 | 395.41 | 22.1 | 96 | 100 | 57.3 |
| PIONEER | 3398 | 164.4 | 18.2 | 399.59 | 21.9 | 98 | 100 | 57.1 |
| Advantage | | −2.8 | 0.5 | −4.18 | 0.2 | −2 | 0 | 0.2 |
| Number of Comparisons | | 37 | 37 | 37 | 20 | 11 | 7 | 36 |
| Percent Wins | | 32 | 64 | 40 | 45 | 18 | 0 | 44 |
| Probability of Difference | | 92 | 97 | 68 | 20 | 63 | 0 | 67 |
| PIONEER | 3394 | 167.1 | 19.4 | 400.61 | 23.6 | 92 | 98 | 56.9 |
| PIONEER | 3379 | 155.0 | 19.4 | 371.71 | 23.7 | 93 | 98 | 56.5 |
| Advantage | | 12.1 | 0.0 | 28.90 | −0.1 | −1 | 0 | 0.4 |
| Number of Comparisons | | 343 | 343 | 343 | 217 | 172 | 122 | 282 |
| Percent Wins | | 85 | 45 | 86 | 41 | 37 | 11 | 52 |
| Probability of Difference | | 99 | 41 | 99 | 44 | 89 | 5 | 99 |
| PIONEER | 3394 | 167.6 | 18.8 | 404.01 | 23.3 | 90 | 99 | 57.0 |
| PIONEER | 3362 | 153.6 | 18.4 | 371.89 | 22.5 | 88 | 99 | 56.4 |
| Advantage | | 14.0 | −0.4 | 32.12 | 0.8 | 2 | 0 | 0.6 |
| Number of Comparisons | | 191 | 191 | 191 | 109 | 90 | 75 | 150 |
| Percent Wins | | 91 | 37 | 92 | 59 | 54 | 2 | 61 |
| Probability of Difference | | 99 | 99 | 99 | 99 | 97 | 35 | 99 |
| PIONEER | 3394 | 170.4 | 19.7 | 407.79 | 24.3 | 95 | 98 | 57.1 |
| PIONEER | 3241 | 161.8 | 22.7 | 375.08 | 23.8 | 94 | 95 | 56.0 |
| Advantage | | 8.6 | 3.0 | 32.71 | 0.5 | 1 | 3 | 1.1 |
| Number of Comparisons | | 130 | 130 | 130 | 95 | 61 | 45 | 105 |
| Percent Wins | | 73 | 96 | 85 | 53 | 47 | 15 | 71 |
| Probability of Difference | | 99 | 99 | 99 | 93 | 54 | 77 | 99 |
| PIONEER | 3394 | 136.4 | 25.9 | 308.72 | 23.2 | 90 | 100 | 55.5 |
| GARST | 8532 | 113.3 | 25.5 | 258.72 | 24.2 | 77 | 100 | 55.0 |
| Advantage | | 23.1 | −0.4 | 50.00 | −1.0 | 13 | 0 | 0.5 |
| Number of Comparisons | | 3 | 3 | 3 | 2 | 2 | 2 | 2 |
| Percent Wins | | 66 | 66 | 66 | 0 | 50 | 0 | 50 |
| Probability of Difference | | 58 | 28 | 60 | 50 | 36 | 0 | 50 |
| PIONEER | 3394 | 168.2 | 22.0 | 392.84 | 20.5 | 95 | 100 | 50.0 |
| WYFFELS | W670 | 149.9 | 23.7 | 344.68 | 25.0 | 92 | 100 | 55.0 |
| Advantage | | 18.3 | 1.7 | 48.16 | −4.5 | 3 | 0 | −5.0 |
| Number of Comparisons | | 6 | 6 | 6 | 1 | 1 | 1 | 1 |
| Percent Wins | | 83 | 83 | 83 | 0 | 100 | 0 | 0 |
| Probability of Difference | | 97 | 84 | 97 | 0 | 0 | 0 | 0 |
| PIONEER | 3394 | 167.9 | 19.3 | 402.93 | 23.6 | 92 | 98 | 56.9 |
| WEIGHTED AVG | | 156.8 | 19.5 | 375.69 | 23.3 | 91 | 98 | 56.7 |
| Advantage | | 11.1 | 0.2 | 27.24 | 0.3 | 1 | 0 | 0.2 |
| Number of Comparisons | | 1114 | 1114 | 1114 | 674 | 521 | 379 | 909 |
| Percent Wins | | 81 | 46 | 82 | 48 | 46 | 7 | 49 |
| Probability of Difference | | 99 | 99 | 99 | 99 | 99 | 81 | 99 |

NOTE: The probability values are useful in analyzing if there is a "real" difference in the genetic potential of the products involved. High values are desirable, with 95% considered significant for real differences.

EXAMPLE 3

Comparison of Key Characteristics for Hybrid 3394

Characteristics of Pioneer Brand Hybrid 3394 are compared to Pioneer Brand Hybrids 3503, 3417, 3398, 3379, 3362, and 3241; Garst Brand Hybrid GR8532; and Wyffel Brand Hybrids WYF627 and WYF670 in Table 3. The ratings given for most of the traits are on a 1–9 basis. In these cases 9 would be outstanding, while 1 would be poor for the given characteristics. These values are based on performance of a given hybrid relative to other Pioneer commercial, precommercial, and competitive hybrids that are grown in research and strip test trials. The traits characterized in Table 3 were defined previously and the ratings utilized not only research data but experience trained corn researchers had in the field as well as sales experience with the hybrids in strip test and the field. These scores reflect the hybrid's relative performance to other hybrids for the characteristics listed. The table shows 3394 yielded well for its maturity, yielding equally well at both high and low plant population densities. 3394 has very good stay green and seedling vigor compared to the other hybrids. 3394 is shorter compared to the other hybrids except Pioneer Hybrid 3241. 3394 has overall excellent yield and agronomic characteristics which should make it an important hybrid in its area of adaptation.

the sample. Applicant imposes no restrictions on the availability of the deposited material from the ATCC; however, Applicant has no authority to waive any restrictions imposed by law on the transfer of biological material or its transpor-

TABLE 3

HYBRID PATENT COMPARISONS--CHARACTERISTICS
Pioneer Hybrid 3394 vs Pioneer Hybrids 3503, 3417, 3398, 3379, 3362, and 3241;
Garst Hybrid 8532; and Wyffel Hybrids WYF627 and WYF670

| HYBRID | SILK_CRM | GDU_SILK | BL_CRM | GDU_BL | CRM | YLD | H/POP | L/POP | D/D | S/L |
|---|---|---|---|---|---|---|---|---|---|---|
| 3394 | 109 | 1442 | 110 | 2760 | 111 | 9 | 9 | 9 | 6 | 7 |
| 3503 | 107 | 1413 | 106 | 2698 | 109 | 8 | 8 | 7 | 5 | 4 |
| 3417 | 108 | 1423 | 110 | 2760 | 108 | 9 | 8 | 9 | 6 | 4 |
| 3398 | 108 | 1435 | 109 | 2756 | 111 | 9 | 8 | 9 | 5 | 6 |
| 3379 | 112 | 1473 | 116 | 2856 | 111 | 8 | 9 | 6 | 8 | 7 |
| 3362 | 111 | 1462 | 110 | 2767 | 111 | 8 | 9 | 6 | 6 | 5 |
| 3241 | 112 | 1478 | 113 | 2806 | 114 | 8 | 8 | 6 | 4 | 8 |
| GR8532 | 105 | | | | 113 | 8 | 8 | 6 | 3 | 4 |
| WYF627 | 108 | 1435 | 108 | 2739 | 111 | 7 | 5 | 7 | 5 | 3 |
| WYF670 | 106 | 1399 | 107 | 2714 | 113 | 7 | 8 | 6 | 3 | 4 |

| HYBRID | R/L | STGR | D/T | T/WT | G/A | S/VIG | P/HT | E/HT | D/E | B/STK |
|---|---|---|---|---|---|---|---|---|---|---|
| 3394 | 7 | 8 | 7 | 5 | 6 | 8 | 5 | 4 | 4 | 4 |
| 3503 | 6 | 6 | 7 | 8 | 6 | 6 | 3 | 3 | 6 | 5 |
| 3417 | 6 | 4 | 8 | 5 | 5 | 5 | 4 | 2 | 6 | 4 |
| 3398 | 6 | 3 | 8 | 5 | 7 | 5 | 4 | 3 | 6 | 6 |
| 3379 | 5 | 7 | 8 | 5 | 5 | 4 | 4 | 5 | 6 | 7 |
| 3362 | 7 | 6 | 9 | 4 | 4 | 4 | 4 | 3 | 6 | 8 |
| 3241 | 4 | 8 | 7 | 5 | 6 | 9 | 7 | 8 | 5 | 3 |
| GR8532 | 7 | 5 | 8 | 5 | 4 | 5 | 2 | 1 | 5 | 7 |
| WYF627 | 3 | 2 | 4 | 4 | 4 | 4 | 4 | 5 | 4 | |
| WYF670 | 7 | 5 | 8 | 5 | 4 | 5 | 2 | 1 | 5 | 7 |

Although the foregoing invention has been described in some detail by way of illustration and example for purposes of clarity and understanding, it will be obvious that certain changes and modifications may be practiced within the scope of the invention, as limited only by the scope of the appended claims.

Deposits

Applicant has made a deposit of at least 2500 seeds of Hybrid Corn Line 3394 with the American Type Culture Collection (ATCC), Rockville, Md. 20852 USA, ATCC Deposit No. 97224. The seeds deposited with the ATCC on July 17, 1995 were taken from the deposit maintained by Pioneer Hi-Bred International, Inc., 700 Capital Square, 400 Locust Street, Des Moines, Iowa 50309–2340 since prior to the filing date of this application. This deposit of the Hybrid Corn Line 3394 will be maintained in the ATCC depository, which is a public depository, for a period of 30 years, or 5 years after the most recent request, or for the effective life of the patent, whichever is longer, and will be replaced if it becomes nonviable during that period. Additionally, Applicant has satisfied all the requirements of 37 C.F.R. §§1.801 - 1.809, including providing an indication of the viability of tation in commerce. Applicant does not waive any infringement of its rights granted under this patent.

What is claimed is:

1. A hybrid corn plant designated as 3394 and its parts, and having ATCC accession number 97224.

2. A tissue culture of regenerable cells of the plant of claim 1 wherein the plants regenerated from the culture have all the physiological and morphological characteristics of 3394.

3. A corn plant regenerated from the tissue culture of claim 2 and having all the physiological and morphological characteristics of hybrid 3394.

4. A tissue culture of a plant according to claim 2, wherein the tissue is selected from the group consisting of leaves, pollen, embryos, roots, root tips, anthers, silk, flowers, kernels, ears, cobs, husks, stalks, cells, and protoplasts thereof.

5. A hybrid corn plant having all the physiological and morphological characteristics of 3394, ATCC accession number 97224.

6. Seed produced by a hybrid corn plant designated as 3394, said hybrid corn plant having ATCC accession number 97224.

* * * * *